United States Patent [19]

Treybig

[11] Patent Number: 4,814,447

[45] Date of Patent: Mar. 21, 1989

[54] PREPARATION OF HYDROXYALKYLPIPERAZINONES BY REACTING AN ALKYLENE OXIDE WITH DECAHYDROPYRAZINO[2,3-B]PYRAZINE OR ITS SUBSTITUTED DERIVATIVES

[75] Inventor: Duane S. Treybig, Lake Jackson, Tex.

[73] Assignee: The Dow Chemical Company, Midland, Mich.

[21] Appl. No.: 85,427

[22] Filed: Aug. 13, 1987

[51] Int. Cl.$^4$ ............................................ C07D 241/08
[52] U.S. Cl. ...................................................... 544/384
[58] Field of Search ........................................ 544/384

[56] References Cited

U.S. PATENT DOCUMENTS

| | | | |
|---|---|---|---|
| 4,246,412 | 1/1981 | Lai | 544/384 |
| 4,292,240 | 9/1981 | Lai et al. | 544/384 |
| 4,621,141 | 11/1986 | Chibnik | 544/384 |

Primary Examiner—Glennon H. Hollrah
Assistant Examiner—James H. Turnipseed
Attorney, Agent, or Firm—A. Cooper Ancona

[57] ABSTRACT

The 4-(2-hydroxyalkyl)-2-piperazinones and their substituted derivatives are prepared by reacting a decahydropyrazino[2,3-b]pyrazine or its substituted derivative having at least one active amine hydrogen, with an alkylene oxide having 2 to 4 carbon atoms.

40 Claims, No Drawings

PREPARATION OF HYDROXYALKYLPIPERAZINONES BY REACTING AN ALKYLENE OXIDE WITH DECAHYDROPYRAZINO[2,3-B]PYRAZINE OR ITS SUBSTITUTED DERIVATIVES

BACKGROUND OF THE INVENTION

The present invention pertains to 4-(2- hydroxyalkyl)-2-piperazinones and their substituted derivatives. The preparation of 4-(2-hydroxyalkyl)-2piperazinones by reacting the appropriate 2-piperazinone or 3-substituted alkyl- or aryl-2-piperazinones with ethylene oxide or ethylene chlorohydrin is known. This early research is disclosed in *Chimie Therapeutique*, May-June, 1969, No. 3, pp. 167–173 and in U.S. Pat. No. 2,633,467. The substituted 4-(2-hydroxyethyl)-2-piperazinones include compounds such as 4-(2-hydroxyethyl)-3-methyl-2-piperazinone and 4-(2- hydroxyethyl)-3,3-diphenyl-2-piperazinone and the like alkyl and aryl substituted 2-piperazinones.

The present invention provides a more economical route for the preparation of the subject compounds in that it is not necessary to make the piperazinone starting reactant of the known art.

SUMMARY OF THE INVENTION

The 4-(2-hydroxyalkyl)-2-piperazinones and their substituted derivatives are prepared by reacting an alkylene oxide wherein the alkylene moiety has 2 to carbon atoms wth a decahydropyrazino2,3-b]pyrazine or its substituted derivative which has the formula,

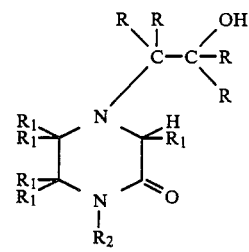

wherein R is hydrogen, an alkyl group having 1-6 carbon atoms or an aryl or aralkyl group having from 6 to 12 carbon atoms, R is hydrogen, an alkyl group having 1-6 carbon atoms or an aryl or aralkyl group having 6 to 12 carbon atoms and $R^2$ is hydrogen, an alkyl group having 1-6 oarbon atoms or an aryl or aralkyl group having 6 to 12 carbon atoms, with the proviso that the compound contain at least one active amine hydrogen.

DETAILED DESCRIPTION OF THE INVENTION

Compounds suitable for reacting with the alkylene oxide and having the above formula are decahydropyrazino[2,3-b]pyrazine and derivatives thereof such as decahydro-1,5-dimethylpyrazino[2,3- C-36,272 -2-b] pyrazine, decahydro-2,6 dimethylpyrazino2,3b-]pyrazine, decahydro-2,2,6,6-tetramethylpyrazino[2,3b-]pyrazine, decahydro-2,3,6,7-tetramethylpyrazino[2,3b-]pyrazine, decahydro-2,2,3,3,6,6,7,7octamethylpyrazino[2,3-b]pyrazine and the like. The preparation of decahydro-pyrazino2,3-b]pyrazine and substituted derivatives thereof is given in U.S. Pat. No. 2,345,237, the teachings of which are incorporated herein by reference.

The 4-(2-hydroxyalkyl)-2-piperazinones which can be made according to the process of the invention include those of the formula:

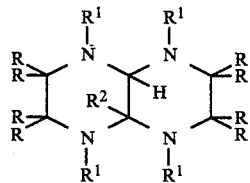

wherein R is hydrogen or an alkyl group having 1 or 2 carbon atoms, R is hydrogen, an alkyl group having 1 to 6 carbon atoms or an aryl or an aralkyl group having from 6 to 12 carbon atoms and R2 is hydrogen, an alkyl or hydroxyalkyl group having from 1 to 6 carbon atoms or an aryl or aralkyl group having from 6 to 12 carbon atoms.

The 4-(2-hydroxyalkyl)-2-piperazinones which can be made by the present process include 4-(2-hydroxyethyl)-2-piperazinone, 4-(2-hydroxyethyl)-1- methyl-2-piperazinone, 4-(2-hydroxyethyl)-5-methyl-2piperazinone, 4-(2-hydroxyethyl)-6-methyl-2piperazinone, 5-ethyl-4-(2-hydroxyethyl)-2-piperazinone, 6-ethyl-4-(2-hydroxyethyl)-2-piperazinone, 4-(2-hydroxyethyl)-5,6-dimethyl-2piperazinone, 1-ethyl-4-(2-hydroxyethyl)-2piperazinone, 4-(2-hydroxyethyl)-5-phenyl-2-piperazinone, 1,4-bis(2-hydroxyethyl)-2-piperazinone, 4-(2- hydroxypropyl)-2-piperazinone, 4-(2-hydroxybutyl)-2piperazinone, and 4-(2-hydroxypropyl)-6-methyl-2piperazinone and the like.

Suitable solvents which can be employed in the reaction are water, alcohols, ethers and the like. Particularly suitable solvents include, water, methanol and ethanol, water being preferred. A solvent is not indispensable, but it minimizes the heat of reaction.

The reaction of an alkylene oxide with decahydropyrazino2,3-b]pyrazine or its substituted derivative is carried out at a temperature between about 0° and about 150° C., preferably between about 25° and about 100° C. Decahydropyrazino2,3-b]pyrazine and its derivatives are solubilized in water and are usually employed in aqueous solution containing more than 5% of the compound when reacted with the alkylene oxide.

The alkylene oxide and decahydropyrazino[2,3-b pyrazine or its substituted derivative can be employed in quantities which provide a mole ratio of alkylene oxide to decahydropyrazino[2,3-b]pyrazine or derivative thereof of from about 0.5:1 to about 4:1, preferably from about 1:1 to about 2:1.

The crude reaction product can be purified by vacuum distillation, solvent extraction, recrystallization or any combination of these techniques. Suitable solvents for extraction include aliphatic hydrocarbons, alcohols, esters and chlorinated solvents. Particularly, suitable solvents include hexane, ethanol, isopropanol, ethyl acetate, methylene chloride and chloroform. Suitable solvents for recrystallization include lower aliphatic ketones and nitriles, eg. acetone and acetonitrile.

The products from the reaction of an alkylene oxide with decahydropyrazino2,3-b]pyrazine, and its substituted derivatives are useful as hydrochloric acid corrosion inhibitors and adhesion promoters. These products also act as binders between asphalt and fiberglass and between asphalt and rock aggregate, comparing favorably with commercial binder products. These utilities are exemplified, and are incorporated herein by reference thereto in a co-filed application, Ser. No. 07/085,428, filed Aug. 13, 1988, entitled "PREPARATION OF HYDROXYALKYLPIPERAZINONES BY REACTING GLYOXAL WITH HYDROXYALKYLDIAMINES". Some may also be useful as regenerative solvents for the absorption of SO₂ from flue gas.

The following example is representative of the method of making the decahydropyrazino-2,3-b]pyrazine and its derivatives, reactants employed in the process of the invention.

EXAMPLE 1

A quantity of 723 g (12 moles) ethylenediamine and 310 g water are weighed into a 2 liter resin kettle equipped with a reflux condenser, an immersion thermometer, an addition funnel and a nitrogen purge system. A solution of 575 g of 30% aqueous glyoxal (3 moles) is placed in the addition funnel and is then added to the diamine solution over a period of about 70 minutes, during which the temperature of the reaction mixture ranges from about 22° to 45° C.

Water is removed by rotary evaporation and a white solid precipitates. The precipitate is filtered, washed with ethanol and allowed to dry. The filtrate is evaporated further and more precipitate collected. This is continued until no more solid material is obtained. The yield of decahydropyrazino[2,3-b]pyrazine is 94.8%.

EXAMPLE 2

Ethylene oxide (20.70 g, 0.5 mole) is added to an aqueous solution of decahydropyrazino[2,3-b]pyrazine (33 g, 0.23 mole) in a citrate bottle at ambient temperature. The temperature rises to approximately 80° C during the ethylene oxide addition. The liquid reaction contents is yellow. Water is removed by rotary evaporation at 100° C. Isopropanol is added and removed by rotary evaporation at 100° C to insure the removal of all water. The product is dissolved in chloroform and filtered through a 14"×1" glass column containing celite. A white solid settles on the celite. The white solid is identified as decahydropyrazino2,3-b]pyrazine by 1H-n.m.r. Chloroform is removed from the filtrate by rotary evaporation. The product is an orange viscous liquid. Gas chromatography indicates this chloroform extracted product contains 38.5% 4-(2-hydroxyethy))-2-piperazinone. Other constituents are identified by gc/ms* as 1,4-bis(2-hydroxyethyl)-2-piperazinone, ethylenediamine, pyrazine, dihydropyrazine, morpholine, 2-[(2aminoethyl)amino]ethanol, N-(2-hydroxyethyl)-dihydropyrazine, N,N'-bis(2-hydroxyethyl)dihydropyrazine and N-(2-hydroxyethyl)morpholine.

*gc/ms indicates analyses made by gas chromatography and mass spectrometry.

In like manner propylene or butylene oxide can be reacted with decahydropyrazino[2,3-b]-pyrazine and derivatives thereof such as decahydro-2,6-dimethylpyrazino[2,3-b]pyrazine, decahydro-2,2,6,6-tetramethylpyrazino2,3-b]pyrazine, decahydro-2,3,6,7-tetramethylpyrazino[2,3-b]pyrazine and decahydro-2,2,3,3,6,6,7,7octamethylpyrazino2,3-b]pyrazine to form 4-(2-hydroxy- propyl)-2-piperazinone, 1,4-bis(2-hydroxypropyl)-2piperazinone, 4-(2-hydroxybutyl)-2-piperazinone, 4-(2 hydroxypropyl -6-methyl-2-piperazinone, 4-(2-hydroxy- butyl)-6,6-dimethyl-2-piperazinone, 4-(2-hydroxybutyl)5,6-dimethyl-2-piperazinone and 4-(2-hydroxypropyl)5,5,6,6-tetramethyl-2-piperazinone, The hydroxyalkyl piperazinone products made according to the above process are known to be corrosion inhibitors.

We claim:
1. A process for the preparation of 4-(2-hydroxyalkyl-2-piperazinones and their substituted derivatives which comprises reacting an alkylene oxide wherein the alkylene moiety has 2 to 4 carbon atoms with a decahydropyrazinol[2,3-b]pyrazine or its substituted derivative having the formula

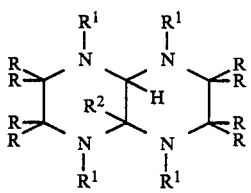

wherein R is independently selected from hydrogen, an alkyl group having 1–6 carbon atoms or an aryl or aralkyl group having from 6 to 12 carbon atoms, $R^1$ is independently selected from hydrogen, an alkyl group having 1–6 carbon atoms or an aryl or aralkyl group having 6 to 12 carbon atoms and $R^2$ is hydrogen, an alkyl group having 1–6 carbon atoms or an aryl or aralkyl group having 6 to 12 carbon atoms, with the proviso that the compound contain at least one active amine hydrogen.

2. The process of claim 1 wherein at least two $R^1$ groups are alkyl and R and $R^2$ are each hydrogen.

3. The process of claim 2 wherein the alkyl group is methyl.

4. The process of claim 3 wherein the compound is decahydro-1,5-dimethylpyrazino2,3-b]pyrazine.

5. The process of claim 1 wherein $R^1$ and $R^2$ are each hydrogen and R is hydrogen or alkyl.

6. The process of claim 5 wherein the alkyl group is methyl.

7. The process of claim 6 wherein the compound is decahydro-2,6-dimethylpyrazino2,3-b]pyrazine, decahydro-2,2,6,6-tetramethylpyrazino2,3-b]pyrazine, decahydro-2,3,6,7-tetramethylpyrazino2,3-b]pyrazine or decahydro-2,2,3,3,6,6,7,7-octamethylpyrazino[2,3-b]pyrazine 8. The process of claim 1 wherein R, $R^1$ and $R^2$ are each hydrogen.

9. The process of claim 1 wherein the alkylene oxide is ethylene oxide.

10. The process of claim 2 wherein the alkylene oxide is ethylene oxide.

11. The process of claim 5 wherein the alkylene oxide is ethylene oxide.

12. The process of claim 8 wherein the alkylene oxide is ethylene oxide.

13. The process of claim 1 wherein the mole ratio of alkylene oxide to decahydropyrazino2,3-b]pyrazine or its substituted derivative is from about 0.5:1 to about 4:1.

14. The process of claim 13 wherein the mole ratio of alkylene oxide to decahydropyrazino2,3-b]pyrazine or its substituted derivative is from about 1 to about 2:1.

15. The process of claim 1 wherein the temperature of reaction is from about 0° to about 150° C.

16. The process of claim 15 wherein the temperature of reaction is from about 25° to about 17. The process of claim 1 wherein the crude reaction product is purified by distillation, extraction, crystallization or a combination thereof.

18. The process of claim 17 wherein the extraction solvent is an aliphatic hydrocarbon, alcohol, ester or a chlorinated solvent.

19. The process of claim 18 wherein the chlorinated solvent contains 1–3 carbon atoms.

20. The process of claim 19 wherein the chlorinated solvent is chloroform.

21. The process of claim 17 wherein the crystallization solvent is an aliphatic ketone or nitrile or mixtures thereof.

22. The process of claim 21 wherein the ketone is acetone and the nitrile is acetonitrile.

23. The process of claim 10 wherein the mole ratio of ethylene oxide to the decahydropyrazino2,3-b]pyrazine or its substituted derivative is from about 0.5:1 to about 4:1.

24. The process of claim 11 wherein the mole ratio of ethylene oxide to the decahydropyrazino2,3-b]pyrazine or its substituted derivative is from about 0.5:1 to about 4:1.

25. The process of claim 24 wherein the mole ratio of ethylene oxide to the decahydropyrazino2,3-b]pyrazine or its substituted derivative is from about 1:1 to about 2:1.

26. The process of claim 23 wherein the temperature of reaction is between about 0° and about 150° C.

27. The process of claim 24 wherein the temperature of reaction is between about 0° and about 150° C.

28. The process of claim 25 wherein the temperature of reaction is between about 0° and about 150° C.

29. The process of claim 23 wherein the crude reaction product is purified by distillation, extraction, crystallization or a combination thereof.

30. The process of claim 24 wherein the crude reaction product is purified by distillation, extraction, crystallization or a combination thereof.

31. The process of claim 25 wherein the crude reaction product is purified by distillation, extraction, orystallization or a combination thereof.

32. The process of claim 29 wherein the extraction solvent is an aliphatic hydrocarbon, alcohol, ester or a chlorinated solvent.

33. The process of claim 30 wherein the extraction solvent is an aliphatic hydrocarbon, alcohol, ester or a chlorinated solvent.

34. The process of claim 31 wherein the extraction solvent is an aliphatic hydrocarbon, alcohol, ester or a chlorinated solvent.

35. The process of claim 23 wherein the crystallization solvent is an aliphatic ketone or nitrile or mixtures thereof.

36. The process of claim 24 wherein the crystallization solvent is an aliphatic ketone or nitrile or mixtures thereof.

37. The process of claim 25 wherein the crystallization solvent is an aliphatic ketone or nitrile or mixtures thereof.

38. The process of claim 32 wherein the extraction solvent is a chlorinated solvent.

39. The process of claim 33 wherein the extraction solvent is a chlorinated solvent.

40. The process of claim 34 wherein the extraction solvent is a chlorinated solvent.

* * * * *